United States Patent [19]

Larson

[11] Patent Number: 4,639,249

[45] Date of Patent: Jan. 27, 1987

[54] LATCH INTEGRAL WITH LATCHED APPARATUS

[76] Inventor: Eldon E. Larson, 7500 Seabeck Holly Rd., NW., Bremerton, Wash. 98312

[21] Appl. No.: 818,477

[22] Filed: Jan. 13, 1986

[51] Int. Cl.[4] .............................................. A61M 5/32
[52] U.S. Cl. .................................................... 604/198
[58] Field of Search ............... 604/196, 197, 198, 208, 604/209, 210, 211, 263

[56] References Cited

U.S. PATENT DOCUMENTS

| 2,888,924 | 6/1959 | Dunmire | 604/197 |
| 3,046,985 | 7/1962 | Saenz | 604/197 |
| 3,487,834 | 1/1970 | Smith, Jr. et al. | 604/197 X |
| 3,890,971 | 6/1975 | Leeson et al. | 604/197 X |

Primary Examiner—John D. Yasko
Attorney, Agent, or Firm—Robert W. Jenny

[57] ABSTRACT

The disclosure relates to a syringe latch apparatus which prevents movement of the syringe piston beyond a certain distance into the cylinder. The latch element is a rectangular segment of the cylinder wall.

8 Claims, 4 Drawing Figures

LATCH INTEGRAL WITH LATCHED APPARATUS

BACKGROUND OF THE INVENTION

1. Field of the Art

The subject invention is in the field of latches which prevent motion of one piece of apparatus relative to another until the latch is operated. More specifically it is in the field of latches used with apparatus in telescopic engagement to prevent telescopic relative motion until the latch is operated.

2. Prior Art

The prior art for this invention, even in the more specific field, is profuse. A most pertinent example, however, is the latch used in an invention by the subject inventor, the invention being the subject of U.S. Pat. No. 4,534,449, entitled "Perforating Seal Greasing Apparatus and Method." Elements are telescopically engaged and a latch prevents relative motion between them. It has been found that the competition in the marketing of inventions, such as that of U.S. Pat. No. 4,534,449, is such that the cost of manufacture of such devices is of unusual significance. This is particularly true when the product is intended in part for non-professional uses undertaken for the express purpose of conserving costs. Therefore, the primary problem leading to the subject invention was the reduction of the costs of manufacture.

It has been recognized that costs can be reduced by manufacturing at least the telescopic parts by injection molding of plastics. It has also been recognized that the costs can be still further reduced by mass production using injection molding and by the reduction of the number of separate parts to be manufactured, assembled, inventoried, etc.

SUMMARY OF THE INVENTION

The subject invention is described in an application of it to apparatus designed to facilitate the injection of the contents of a standard 3 cc medical syringe into a cavity through an elastomeric covering of the cavity. The apparatus essentially comprises two telescopic parts, a cylinder component and a piston component telescopically fitted into the cylinder component. The piston of the piston component is hollow and the syringe fits into the piston with its needle extending through the end of the piston which is inserted into the cylinder. The depth of insertion of the piston into the cylinder is limited by the subject latch apparatus until the latch is operated. At this limited insertion depth the needle of the syringe is enclosed in a cylindrical shroud which is part of the cylinder component with the tip of the needle just inside the tip of the shroud. A compression spring is installed to keep the piston positioned so that the needle is protected by the shroud until the latch is operated.

The syringe is itself a telescopic apparatus having a cylinder and piston. One end of the cylinder is fitted with the injection needle and the piston extends from the other end of the cylinder.

There are commercially available syringes which are expendable and in which the needle assembly is attached to the cylinder by a threaded connection. In a preferred embodiment of the subject invention the needle assembly is retained in the piston assembly by a friction fit and the syringe cylinder and piston are removed from it and attached to it by means of the threaded connection in the process of using a plurality of lubricant filled syringes to lubricate a corresponding plurality of items. This feature further reduces costs by making it unnecessary to provide an expendable needle assembly for each application of the contents of a syringe, such as lubrication.

In operation the shroud is located at the position in which the injection is to be made. In doing so some force may be applied on the piston of the syringe provided that the force is insufficient to overcome the friction between the syringe piston and syringe cylinder. This force is sufficient, however, to move the piston of the apparatus into the cylinder of the apparatus against the force of the compression spring and as far as the latch will permit. Operation of the latch then permits the piston of the apparatus to move into the apparatus cylinder until it bottoms in the cylinder. With this motion the syringe needle extends beyond the shroud and into the cavity into which the contents of the syringe are to be injected. Continued pressure on the syringe piston then moves that piston into the syringe cylinder to expel the contents into the cavity. It is clear from this description that in this arrangement the force required to overcome the friction between the syringe piston and cylinder is greater than the force needed to overcome the compression spring force and thrust the syringe needle through the covering of the cavity and into the cavity.

With this apparatus and its operation understood, the latch apparatus itself can now be described. The latch element which serves to prevent movement of the piston beyond a certain distance into the cylinder is a segment of the cylinder wall. The segment is rectangular. Its width is transverse to the axis of the cylinder and is a fraction of the cylinder diameter, 1/6 being a preferred value. Its length is a multiple of its width, 6 being a preferred value. The rectangular segment is separated from the cylinder wall along its two long sides by slits and across one end, the end nearest the end of the cylinder into which the piston is inserted. The other, unseparated end of the segment functions as a spring hinge so that the segment is a leaf spring. In the molding of the apparatus the segment is biased so that its free end is set far enough toward the center line of the cylinder to engage the end of a rim on the piston. Engagement of the latch and rim prevents the needle from extending beyond the end of the cylinder until the latch is operated.

The mechanism which is operated to move the free end of the latch segment in the direction away from the center line of the cylinder, in order to allow further motion of the piston, is molded integrally with the cylinder and the segment. The apparatus comprises a thin strip of material as wide as the segment, extending across its free end and away from and essentially at a right angle to the cylinder center line. The strip extends only a short distance from the outer surface of the segment and serves as a hinge element to connect, to the segment, the lever which operates the latch segment.

The lever comprises two surfaces essentially at right angles to each other and emanating from the juncture of the hinge strip and the lever. A first surface extends outwardly from the cylinder center line in a plane essentially perpendicular to the center line. The end of this surface, farthest from the center line, is the tip of the lever and this surface is called the force surface. The second surface extends parallel to the cylinder center line and contacts the cylindrical surface on the rim of the piston beyond the latching surface. The end of the second surface, in contact with the land, serves as the fulcrum of the lever. This second surface is called the fulcrum surface. Force applied to the force surface at the tip of the lever in a direction essentially parallel to the cylinder center line and away from the needle end of the apparatus rotates the lever about the fulcrum and, via the hinge element, moves the end of the latch segment radially out of the way of the latching surface of the rim. The piston is thus freed for the piercing motion, followed by the injection motion of the syringe piston into the syringe cylinder.

To complete the operation, the apparatus is removed from the injected cavity covering, the compression spring moves the apparatus piston to its start position and the latch re-engages the rim. The syringe (or the cylinder/piston portion of it) is removed and replaced by another if the operation is to be repeated.

The apparatus has been described with one latch. In a preferred embodiment there are two, located diametrically opposite to each other on the cylinder. Use of three or more latches is also possible.

DETAILED DESCRIPTION OF THE INVENTION

Figure 1:
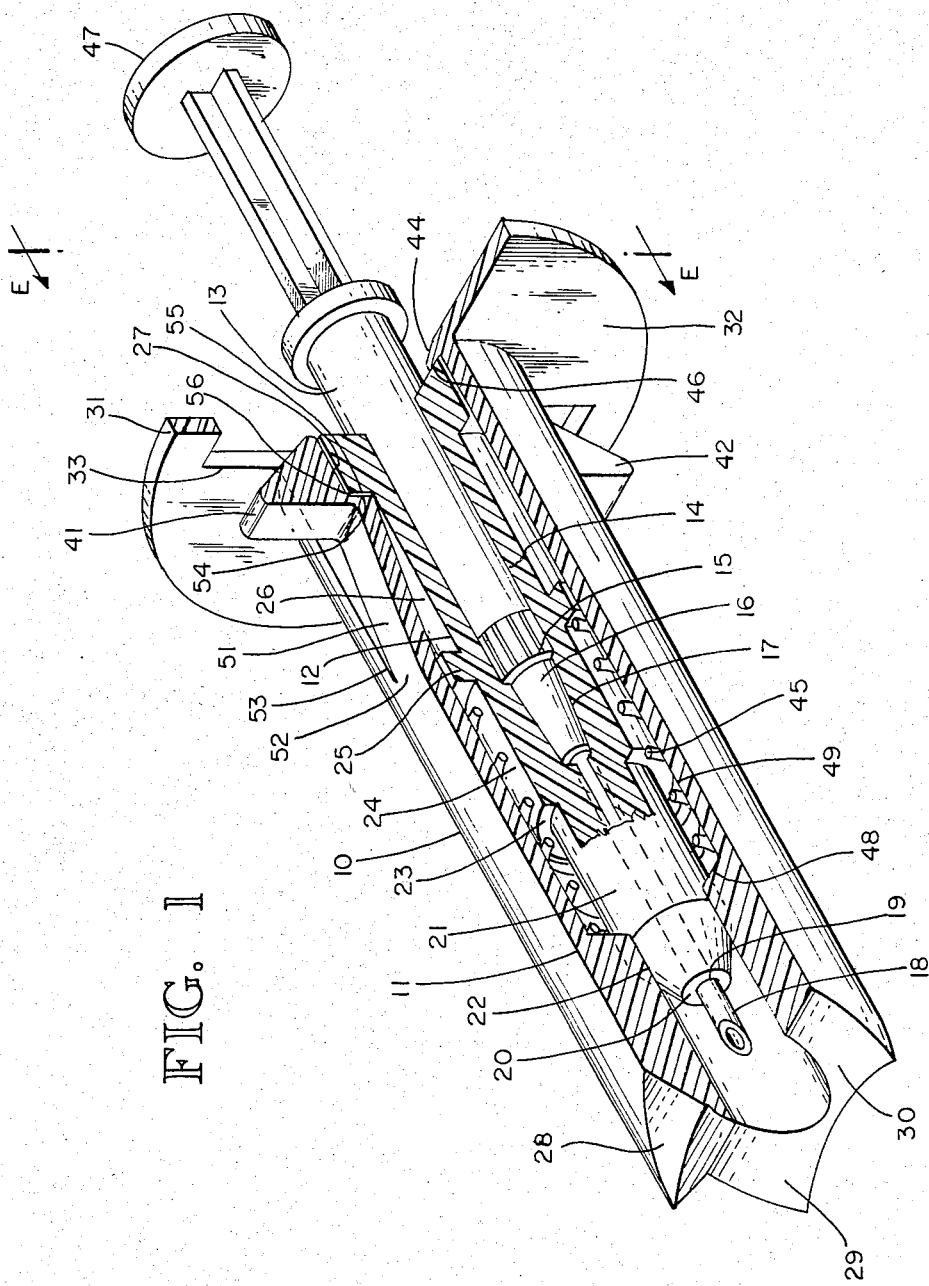
FIG. 1 is a sectioned perspective view of apparatus into which the subject latch is incorporated.

Referring to FIG. 1, the apparatus 10 incorporating the subject latch comprises a cylinder component 11 and a piston component 12. The piston component is hollow and a standard 3 cc syringe assembly 13 fits into bore 14 with needle base 15 of needle assembly 16 frictionally grasped in tapered section 17 in the piston component. Needle 18 of the needle assembly extends through hole 19 in the piston component and beyond end 20 of the piston component. The extent of this extension determines the distance the needle will penetrate into the cavity which receives the contents of the syringe. As is well known in the art, needle assembly 16 is integrated with the syringe assembly by a threaded connection. With the needle assembly held by friction in the piston component, the remainder of the syringe assembly can be removed from and installed in the piston component by threading it off of and onto the needle assembly. With this procedure costs can be reduced since one needle assembly can be used repeatedly instead of requiring a needle assembly for each use.

The exterior of the piston component comprises (1) cylindrical surface 21, which engages bore 22 of the cylinder component in sliding contact, (2) shoulder 23 between surface 21 and (3) cylindrical surface 24, (4) flange 25, (5) cylindrical surface 26 which has the same diameter as surface 24 and (6) land 27.

The exterior of the cylinder component is essentially cylindrical. End 28 is specially shaped with a V-shaped groove 29 positioned across the end perpendicular to the longitudinal axis of the cylinder. The angle of the V in this embodiment is 45 degrees and the lip(s) 30 of the groove extend slightly beyond the surface of bore 22.

End 31 of the cylinder component comprises flange 32 which is flat and perpendicular to the longitudinal axis of the cylinder.

Figure 2:
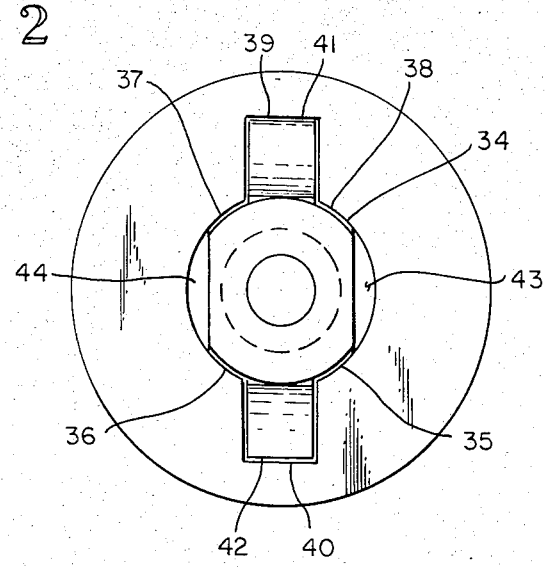
FIG. 2 is a view of end E of the apparatus of FIG. 1.

Referring to FIGS. 1 and 2, flange 32 is made with a specially shaped opening 33. Surfaces 34, 35, 36 and 37 are portions of a cylindrical hole 38 having a diameter slightly larger than the diameter of land 27 of the piston component. Parts 39 and 40 are rectangular extensions of the opening, sized and positioned to allow levers 41 and 42, described in detail later, to pass through flange 32. Parts 43 and 44 are sloped so that flange 25 and land 27 will, by camming action, spread the flange 32 to allow entry of the piston component into the cylinder component. Compression spring 45 is inserted into the cylinder component before the insertion of the piston component and both insertions involve the camming described above and displacement of levers 41 and 42 and associated latch apparatus as described in more detail later. Once the piston component is fully inserted, surface 46 and its opposite, not shown in FIG. 1, hold it in place against the force of spring 45.

In operation, end 28 of the cylinder component is positioned on the work piece into which the contents of the syringe are to be injected. Force is then applied to head 47, tending to move the piston component into the cylinder component and to actuate the syringe. However, the friction force required to actuate the syringe is greater than the combination of forces needed to move the piston component against the force of the compression spring 45 and the force needed to cause the needle to pierce the cover of the cavity of the work piece. To enable the motion of the piston component into the cylinder component, latch action is required by the latching features which are the essence of the subject invention. These features are described in reference to the latch shown in FIG. 1, the other not being fully visible in the drawing.

When the latch has been operated, the piston component will be free to move into the cylinder component until surface 48, the juncture of bores 22 and 49 on the interior of the cylinder component, is contacted by shoulder 23.

The latch element is a cantilever spring 51, attached to the cylinder wall at 52, separated from the cylinder wall on each of its sides by slit(s) 53 (only one slit shown because of sectioning) and formed to deflect toward the center of the cylinder component so that its end 54 abuts face 55 of land 27 to prevent motion of the piston component further into the cylinder component until end 54 is moved out of position. The effective length of spring 51 is from attachment point 52 to end 54. Levers 41 and 42 are hinged to the cantilever spring latch elements, lever 41 being shown hinged to spring 51 in FIG. 1. The hinging is provided by the relatively thin portions of material 56 and 57 (not shown) which interconnect the levers and springs.

Figure 3A:
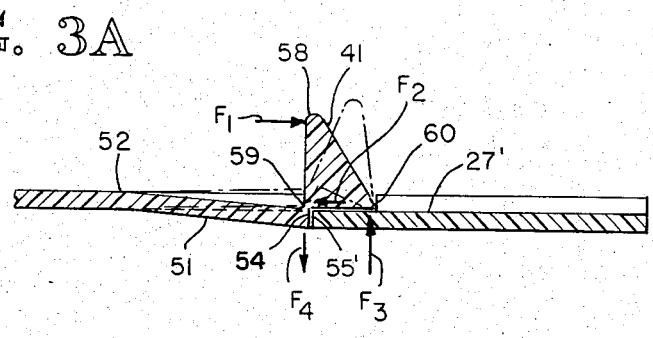
FIG. 3A is a schematic view of the latch with the fulcrum surface operating on a surface on the piston with the lever extending through a slot in the cylinder wall as illustrated in FIG. 1.

The lever and unlatching operation is described with reference to FIG. 3A. Force $F_1$, applied as indicated to tip 58 of lever 41 and resisting force $F_2$ at the hinge line 59 produce a torque tending to rotate lever 41 around the hinge line with tip 58 moving in the direction of force $F_1$. This torque is opposed by a torque produced by force $F_3$ at the point of contact between corner 60 of lever 41 and land 27' (equivalent to land 27 in FIG. 1) and force $F_4$ at hinge line 59. The torque produced by forces $F_1$ and $F_2$ overcomes that produced by forces $F_3$ and $F_4$ because of the compliance of spring 51. This compliance allows end 54 to move radially outward from the centerline of the apparatus until it clears face 55' of land 27' and allows the piston element to move further into the cylinder element. The positions of lever 41 and spring 51 after the compliance are indicated in phantom lines in FIG. 3A.

Release of force $F_1$ and force on head 47 allows spring 45 to return the apparatus to the condition shown in FIG. 1, with 51 and its opposing counterpart returning to positions to restrain the piston element again until the unlatching process is repeated.

Figure 3B:
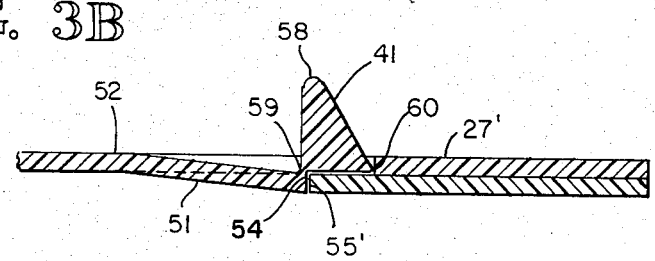
FIG. 3B is a schematic view of the latch with the fulcrum surface operating on a surface on the piston with the lever extending through a gap in the cylinder.

FIG. 3B shows an alternate form of the latch apparatus. In FIG. 3A, corresponding to FIG. 1, the lever 41 is in a slot formed in the cylinder element and the fulcrum surface operates on an outer surface of the piston element. In FIG. 3B, the slot does not extend to the end of the cylinder but, instead, is just large enough to provide clearance for the lever.

In normal operation, the forces are applied to the levers by the index and middle fingers and to head 47 by the thumb (end or base) of the operator's hand.

The described embodiment utilizes two latches. One latch could be sufficient or more than two could be used.

It is considered to be clear from the above description that the subject invention meets its objectives. The telescopic elements of the apparatus can be manufactured as injection molded plastic parts and the latch apparatus is integral with these parts.

A preferred embodiment of the subject invention is described herein. It will be understood that other embodiments and modifications of the one described are possible within the scope of the invention, the scope being limited only by the appended claims.

What is claimed is:

1. An apparatus comprising first and second elements made of resilient material and in sliding contact with each other, said second element being movable in a first direction with respect to said first element and in a second direction opposite to said first direction and having a face surface essentially perpendicular to said first and second directions, latch apparatus comprising:
 a rectangular leaf spring integral with said first element and having:
  a first side,
  a second side,
  a first end, and
  a second end and
  a width W, the distance from said first side to said second side,
 said first and second sides being essentially parallel to said first and second directions, said first side being separated from said first element by a first slit having a width w1 and said second side being separated from said first element by a second slit having a width w2,
 said second end being separated from said first element by a slit having a width w3,
 said first end being integral with said first element and being located a distance L in said first direction from said second end, L being the effective length of said leaf spring and of said first and second slits,
 said leaf spring being formed so that said second end is positioned to abut said face surface of said second element, whereby said second element is prevented from moving in said first direction relative to said first element, means for deflecting said leaf spring to move said second end out of abutment with said face surface, whereby said second element is freed for sliding motion in said first direction relative to said first element.

2. The apparatus of claim 1 in which (1) said first element further comprises a first outer surface and an inner surface, said inner surface being in said sliding contact with said second element, said first outer surface being the outer surface of said first element in which said leaf spring further comprises a second outer surface which is a continuation of said first outer surface and extends from said first side to said second side and from said first end to said second end of said leaf spring,
 in which (2) said second element has a third outer surface, this surface being in sliding contact with said inner surface of said first element and
 in which (3) said width w3 of said slit separating said second end of said leaf spring from said first element is greater than said distance t and
 in which (4) said means for deflecting said leaf spring comprises a hinge and a lever and,
 said hinge being a membrane extending across said second end from said first side to said second side and essentially normal to said second outer surface, said membrane having a length and extending to a juncture with said lever,
 said lever extending from said juncture and comprising:
  a force face extending essentially perpendicular to said second outer surface and
  a fulcrum face extending from said juncture essentially perpendicular to said force face in said second direction,
 said force face having a first tip,
 said fulcrum face having a second tip, said second tip being a distance t from said juncture,
 said length of said membrane being such that said fulcrum face lies in close proximity to said third outer surface,
 whereby a force applied to said first tip in a direction parallel to said second direction and in the direction of said second direction causes rotation of said lever about said hinge and said rotation is resisted by force on said lever from contact of said second tip on said third outer surface, said force being transferred to said hinge and thereby to said second end to deflect said second end out of abutment with said face surface.

3. The apparatus of claim 1 in which said first element has an end perpendicular to said second direction, said end being located a distance from said second end of said leaf spring in said second direction, said first element being slotted from said second end of said leaf spring to said end of said first element, said slot having a width W equal to the sum of said widths w, w1 and w2.

4. The apparatus of claim 3, in which (1) said first element further comprises a first outer surface and an inner surface, said inner surface being in said sliding contact with said second element, said first outer surface being the outer surface of said first element in which said leaf spring further comprises a second outer surface which is a continuation of said first outer surface and extends from said first side to said second side and from said first end to said second end of said leaf spring, and in which (2) said second element has a third outer surface, this surface being in sliding contact with said inner surface of said first element, and in which (3) said means for deflecting said leaf spring comprises a hinge and a lever, said hinge being a membrane extending across said second end from said first side to said second side and essentially normal to said second outer surface, said membrane having a length and extending to a juncture with said lever, said lever extending from said juncture and comprising:

a force face extending essentially perpendicular to said second outer surface and a fulcrum face extending from said juncture essentially perpendicular to said force face in said second direction, said force face having a first tip, said length of said membrane being such that said fulcrum face lies in close proximity to said third outer surface, whereby a force applied to said first tip in a direction parallel to said second direction and in the direction of said second direction causes rotation of said lever about said hinge and said rotation is resisted by force on said lever from contact of said second tip on said third outer surface, said force being transferred to said hinge and thereby to said second end to deflect said second end out of abutment with said face surface.

5. The apparatus of claim 1 in which said first and second elements are in telescopic engagement, said first element being a cylinder element and said second element being a piston element.

6. The apparatus of claim 2 in which said first and second elements are in telescopic engagement, said first element being a cylinder element and said second element being a piston element.

7. The apparatus of claim 3 in which said first and second elements are in telescopic engagement, said first element being a cylinder element and said second element being a piston element.

8. The apparatus of claim 4 in which said first and second elements are in telescopic engagement, said first element being a cylinder element and said second element being a piston element.

* * * * *